United States Patent [19]

Butler et al.

[11] Patent Number: 5,352,697

[45] Date of Patent: Oct. 4, 1994

[54] STORAGE STABLE PESTICIDE COMPOSITIONS COMPRISING AZADIRACHTIN AND EPOXIDE

[75] Inventors: Brett J. Butler, Concord, Calif.; William P. Ellenberger, Salem, Utah; Barry A. Omilinsky, Trenton, N.J.

[73] Assignee: AgriDyne Technologies, Inc., Salt Lake City, Utah

[21] Appl. No.: 920,800

[22] Filed: Jul. 28, 1992

[51] Int. Cl.$^5$ .................. A01N 43/08; A01N 37/00
[52] U.S. Cl. ................... 514/468; 514/558; 514/559; 514/560; 424/DIG. 8
[58] Field of Search ............ 514/468, 558–568, 514/453; 424/DIG. 8

[56] References Cited

U.S. PATENT DOCUMENTS

| | | | |
|---|---|---|---|
| 3,867,526 | 2/1975 | Hennarf et al. | 514/136 |
| 3,962,415 | 6/1976 | Hennarf et al. | 424/40 |
| 3,962,428 | 6/1976 | Emodi | 514/475 |
| 4,281,014 | 7/1981 | Yaffe | 424/285 |
| 4,556,562 | 12/1985 | Larson | 424/195.1 |
| 5,001,146 | 3/1991 | Carter | 514/453 |
| 5,001,149 | 3/1991 | Klocke | 514/468 |

OTHER PUBLICATIONS

Morgan, E. D. (1980) Natural Pesticides form the Neem Tree, Proc. 1st Int'l. Neem Conf., p. 45.
Ley, S. V. (1989) Tetrahedrom 45:2143.
Ley, S. V. (1987) Pesticide Sci. Biotechnol., Proc. Int'l. Cong. Pestic Chem. chem. 6th, pp. 25–35.

*Primary Examiner*—John W. Rollins
*Attorney, Agent, or Firm*—Greenlee and Winner

[57] ABSTRACT

Storage-stable pesticide compositions comprising azadirachtin or an azadirachtin derivative as the active ingredient and an epoxide as the stabilizing agent.

22 Claims, No Drawings

STORAGE STABLE PESTICIDE COMPOSITIONS COMPRISING AZADIRACHTIN AND EPOXIDE

BACKGROUND OF THE INVENTION

The present invention relates to storage-stable pesticide compositions and to methods for their preparation. In particular, the invention relates to storage-stable pesticide compositions containing azadirachtin as the active ingredient and an epoxide, preferably an epoxidized vegetable oil, as the stabilizing agent.

Extracts of the neem tree (*Azadirachta indica*) and the chinaberry tree (*Melia azedarach*) have long been known to have insecticidal activity (Natural Pesticides from the Neem Tree, Proc. 1st Int'l Neem Conf. 1980, 129 (H. Schmutterer, et al. eds. 1981)); Natural Pesticides from the Neem Tree and Other Tropical Plants, Proc. 2nd Int'l Neem Conf. 1983 (H. Schmutterer and K. R. S. Asher eds. 1984); Natural Pesticides from the Neem Tree and Other Tropical Plants, Proc. 3rd Int'l Neem Conf. 1986 (H. Schmutterer and K. R. S. Asher eds. 1987)). The active ingredient of the neem and chinaberry extracts, azadirachtin, is a limonoid of the tetranortriterpenoid type. Azadirachtin has been shown to be a potent insect growth regulator and feeding deterrent (Yamasaki, R. B., et al. (1987) J. Agric. Food Chem. 35:467–471).

Azadirachtin is a large and complex molecule. Its molecular weight is 720, and it has a number of reactive functional groups (including ester, epoxide, and vinyl ether moieties) which render the compound unstable under a variety of conditions. Azadirachtin is reported to decompose in the presence of acids, bases and water. E. D. Morgan, "Strategy in the Isolation of Insect Control Substances from Plants," Natural Pesticides from the Neem Tree, Proc. 1st Int'l Neem Conf. 1989, 45 (H. Schmutterer, et al. eds. 1981); S. V. Ley, et al. (1989) Tetrahedron 45:2143; S. V. Ley, "Synthesis of Insect Antifeedants," Pesticide Sci. Biotechnol., Proc. Int'l Cong. Pestic. Chem. 6th, 25–35 (R. Greenhalgh and T. R. Roberts, eds., 1987); J. A. Klocke, et al., U.S. Pat. No. 5,001,149; Fessenden and Fessenden, *Organic Chemistry*, 2nd Ed., 297,628 (1982); Morrison and Boyd, *Organic Chemistry*, 3rd Ed., 564, 675–684 (1974); G. F. Woods, Jr. (1955) Org. Syn. 3:470; M. Shiraishi and S. Terao (1983) J. C. S. Perkin I, 1591; and T. W. Greene, *Protective Groups in Organic Synthesis*, 21 (1981). In addition, J. B. Stokes and R. E. Redfern (1982) J. Environ. Sci. Health 17 (1):57–65, report rapid degradation of azadirachtin by heat and sunlight. K. Ermel, et al., Proc. 3rd Int'l Neem Conf. 1986, 171 (H. Schmutterer and K. R. S. Asher eds. 1987), report that azadirachtin rapidly decomposes in neem kernels stored at 60° C. under humid, as compared to dry, conditions.

Chemical instability poses a serious impediment to the use of azadirachtin as a pesticidal agent. In short, the molecule tends to have a short shelf life in technical and formulated forms, as prepared by those skilled in the art. Short shelf life, in turn, poses problems for building and storing inventories, carrying product over from one year to the next, and guaranteeing product potency in the consumer's hands. To avert these problems, most chemical pesticide manufacturers require that their products have shelf lives of 2–3 years or more. Azadirachtin does not meet this criterion under most conditions. As such, means for improving the molecule's stability and, hence, its shelf life are of considerable commercial importance.

Storage-stable azadirachtin formulations and methods for preparing stable azadirachtin compositions have been proposed. U.S. Pat. No. 4,556,562 reports that the stability of azadirachtin in ethanol emulsions increases by diluting the concentration of azadirachtin to between 2000 and 4000 ppm and adjusting the pH to between 3.5 and 6.0. U.S. Pat. No. 5,001,146 discloses that azadirachtin stability is improved adjusting the concentration of polar aprotic solvent to at least 50% by volume and by decreasing water content to less than 15% by volume. Both of these prior art formulations were prepared to contain very low concentrations of azadirachtin (0.2–0.4% and 0.3% respectively). This fact places severe constraints on product composition, quality, utility, and consumer acceptance. Pesticides containing low concentrations of active ingredient must be applied at correspondingly high volumes in order for efficacy to be achieved. As such, high volumes of product must be manufactured, shipped, and stored. This factor adds to the costs incurred by manufacturers, distributors, and end users. Moreover, U.S. Pat. No. 5,001,146 teaches that azadirachtin stability depends upon the type of solvent employed, and that stability requires storage in certain enumerated aprotic and alcohol solvents. This factor constrains the use of a broader range of formulation ingredients, many of which are desirable from perspectives of product cost, product performance, user safety, and environmental compatibility.

It is known in the art that various antioxidants, inhibitors and scavengers can stabilize pesticidal compounds against spontaneous decomposition. It is further known in the art that addition of an epoxide compound to N-aminosulfenylated derivatives of carbofuran (U.S. Pat. No. 4,281,014), organophosphate (U.S. Pat. No. 3,867,526) and chlorinated hydrocarbon (U.S. Pat. No. 3,952,102) pesticides increases their shelf life. In general, however, different classes of chemical compounds require different stabilizers because mechanisms of decomposition vary from one pesticide class to the next (U.S. Pat. No. 4,281,014). Selection of a stabilizer is therefore an empirical process.

Azadirachtin is a biologically derived natural product obtained as a complex mixture of compounds by extraction from the seeds of the neem tree. It does not contain N-aminosulfenylated carbofuran, organophosphate or chlorinated hydrocarbon type functional groups found in the synthetic compounds previously mentioned. Nevertheless, it has been unexpectedly found that the stability of azadirachtin in solution is enhanced by the presence of an epoxide, preferably an epoxidized vegetable oil. Use of such an additive improves the stability of pesticide compositions containing a wide range of concentrations (including high concentrations) of azadirachtin. It also permits formulation in a broader range of solvents and other adjuvants that contribute to product performance and safety.

SUMMARY OF THE INVENTION

In accordance with the present invention there is provided a novel pesticide composition comprising azadirachtin as the active ingredient.

Another object of this invention is to provide a storage-stable pesticide composition containing azadirachtin as the active ingredient wherein the composition is stable at a variety of azadirachtin concentrations and wherein the stability is independent of the solvent system.

Yet another object of this invention is to provide a storage-stable pesticide composition containing an azadirachtin derivative as the active ingredient wherein the composition is stable at a variety of azadirachtin derivative concentrations and wherein the stability is independent of the solvent system.

The present invention thus provides a storage-stable pesticide composition comprising azadirachtin or an azadirachtin derivative as the active ingredient and an epoxide as the stabilizing agent. The epoxide protects azadirachtin and azadirachtin derivatives from chemical reactions, thereby stabilizing the compounds, even at low epoxide concentrations. The epoxide stabilizing effect occurs in a variety of solvent systems and at various azadirachtin concentrations.

The present invention also relates to methods for preparing storage-stable azadirachtin extracts and formulations wherein the extracts and formulations are characterized by the presence of an epoxide as a stabilizing agent, particularly an epoxidized vegetable oil.

The primary advantage of the present invention is therefore the improved shelf life of azadirachtin pesticide compositions. The stabilizing effect of epoxides is surprisingly and unexpectedly superior to that of other stabilizing agents. Epoxides, particularly epoxidized vegetable oils, are also inexpensive, non-toxic and readily available in commerce.

Azadirachtin formulations of the present invention, by virtue of the epoxide stabilizing agent, offer improved stability and wider applicability over prior art formulations. Specifically, stabilization by an epoxide eliminates the prior art requirement of low azadirachtin content, thus allowing stabilization of formulations with a wide range of azadirachtin concentrations. Stabilization by an epoxide is also independent of solvent type, thus reducing or eliminating the solvent restrictions of prior art formulations.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The present invention relates to storage-stable pesticide compositions and to methods for their preparation. More particularly, the invention relates to storage-stable pesticide compositions containing azadirachtin and azadirachtin derivatives as the active ingredients and an epoxide as the stabilizing agent.

As used herein, "storage stable" means that the stability of azadirachtin is improved in the presence of the stabilizing agent relative to the stability of azadirachtin without stabilizing agent. In the examples shown, the loss of azadirachtin in formulations comprising epoxidized soybean oil is less than the loss of azadirachtin in formulations without epoxidized soybean oil. The term "extracting agent," as used herein, refers to a selective liquid solvent or combination of solvents capable of separating azadirachtin from other neem seed components. The extracting agent is either an azadirachtin-soluble solvent (or combination of solvents) or a series of solvents having different azadirachtin solubilities, e.g., an azadirachtin-insoluble solvent followed by an azadirachtin-soluble solvent. The term "stabilizing agent," as used herein, refers to compounds which increase the stability of azadirachtin. The stabilizing agents of the present invention fall within the chemical class of epoxides, compounds containing the three-membered oxirane ring.

Epoxide stabilization in accordance with the present invention is effective with limonoid pesticide compositions in general and particularly applicable to compositions containing azadirachtin and azadirachtin derivatives. The invention is characterized by adding epoxide to an azadirachtin containing composition, wherein the azadirachtin is derived from neem seeds. The azadirachtin composition of the present invention can originate from other natural sources or from organic chemical synthesis.

While the mechanism of azadirachtin stabilization by epoxides is not fully understood, and not wishing to be bound by any specific theory, it is believed that the epoxide protects azadirachtin and azadirachtin derivatives from chemical reactions involving the reactive functional groups (e.g., vinyl ether, ester and epoxide moieties). In accordance, azadirachtin derivatives containing any of these functional groups are stabilized by the presence of an epoxide and are therefore encompassed by the present invention. Azadirachtin derivatives containing these functional groups include, but are not limited to, dihydroazadirachtin, tetrahydroazadirachtin, 3-deacetylazadirachtin, 11-methylazadirachtin, 11-acetylazadirachtin, 23-α-ethoxy-22,23, -dihydroazadirachtin, 23-β-ethoxy-22,23-dihydroazadirachtin, 23-α-methoxy-22,23-dihydroazadirachtin, 23-β-methoxy-22,23-dihydroazadirachtin, 23-α-isopropoxy-22,23-dihydroazadirachtin, 23-β-isopropoxy-22,23,-dihydroazadirachtin, 22,23-dihydro-22-α-bromo-α,β-methoxyazadirachtin, 22,23-dihydro-22-α-bromo-α,β-ethoxyazadirachtin, 22,23-dihydro-α-bromo-α,βisopropoxyazadirachtin, 23-α-acetoxy-22,23-dihydroazadirachtin, 23-β-acetoxy-22,23-dihydroazadirachtin 1-cinnamoylazadirachtin, 4-decarbomethoxyazadirachtin, 12-decarbomethoxyazadirachtin, 3-tigloylazadirachtol, tetrahydro-3-tigloylazadirachtol, 1-detigloyl-29-decarbomethoxyazadirachtin, azadirachtol, dihydroazadirachtol, 23-acetoxy-22,23-dihydroazadirachtol, 11,20-0, 0-dicarbomethoxy-22,23-dihydroazadirachtin, 7,11,20-0,0,0-trimethylazadirachtin, 12,29-didecarbomethoxyazadirachtin, 3-tigloyl-13,14-deepoxyazadirachtol, and 1-hydroxy-3-tigloyl-19-demethyleneoxyazadirachtin. This list is by way of illustration only and is not intended, in any way, to be limitative thereof. Azadirachtin derivatives of the present invention are derived from plants of the family Meliceae, by modifications of naturally occurring limonoid compounds, and by chemical synthesis.

The storage-stable pesticide compositions of this invention are prepared by dissolving a material containing the active ingredient (an azadirachtin or azadirachtin derivative) in suitable solvent or solvent combination and adding a stabilizing agent to the solution. Suitable solvents are known to those skilled in the art, and the choice of a particular solvent is not critical to the invention. That is, epoxides enhance the stability of azadirachtin in a wide variety of solvent systems.

In a second embodiment, a stabilizing agent is added to an extracting agent during and/or after extraction of azadirachtin from coarsely ground neem seed. Azadirachtin extraction can be accomplished by methods known in the art. If desired, the neem oil is first removed from the neem seeds with an azadirachtin-insoluble solvent, followed by extraction of azadirachtin from the defatted neem seeds with an azadirachtin-soluble solvent. Alternatively, azadirachtin and neem oil are extracted together with an azadirachtin-soluble solvent. An epoxide, preferably epoxidized vegetable oil, is added during and/or after extraction to form a storage-stable azadirachtin composition.

A surfactant or surfactant blend is preferably included in the composition to promote uniform dispersion of the ingredients in carriers. The surfactant concentration generally depends on the particular surfactant, the solvent used, and the concentration of the active ingredient desired. The surfactant concentration typically ranges from about 0.2% to about 50%, and preferably from about 3% to about 20% Suitable surfactants are known to those skilled in the art and are readily available in commerce. The choice of a particular surfactant is not critical to the invention. Preferred surfactants include anionic and non-ionic compounds such as, but not limited to, sorbitan fatty acid esters, ethoxylated sorbitan esters, glycerol esters, ethoxylated mono-, di- or triglycerides, ethoxylated alcohols, ethoxylated alkyl phenols, dodecyl benzene sulfonic acid and its salts, and ethylene oxide and/or propylene oxide block polymers. Surfactant blends containing anionic and non-ionic compounds are also preferred.

Levels of azadirachtin decomposition are directly correlated with temperature and time as governed by chemical kinetics. Specifically, high levels of decomposition are typically associated with high temperatures and long periods of time. By convention, the pesticide industry typically uses accelerated aging studies to test the relative stability of various product formulations. In such tests, high temperatures (30°–80° C.) are used to accelerate decomposition reactions so that the stabilities of test formulations can be compared over a relatively short period of time (1–6 months). Results of such tests are often used to predict relative stabilities of products at lower temperatures (20°–30° C.) over longer periods of time (1–3 years).

In the present invention, accelerated aging tests have been used to compare the stability of azadirachtin in various pesticide compositions containing different solvents, with and without different surfactant blends, and with and without epoxides. Several important results are evident.

First, in the absence of epoxides, azadirachtin decomposes in solutions, and relative to other pesticidal compositions, it realizes a short shelf life. As shown in Example 1, decomposition occurs across a variety of solvent types, although the absolute rate of decomposition varies between the particular solvents. Addition of various commercial surfactant blends, typically included in azadirachtin formulations, also significantly increases the rate of decomposition (Example 2).

Second, and most importantly, azadirachtin compositions containing epoxidized soybean oil retain substantially more azadirachtin in accelerated aging tests than compositions which contain no added epoxides or that contain non-epoxidized paraffinic oil ("crop oil"). The effect of adding epoxidized soybean oil is most evident as temperatures increase to 37°–43° C. and beyond (Example 5).

That addition of an epoxide enhances the stability of azadirachtin in solution is surprising and unexpected. This is true: (1) in view of the fact that the mechanisms of azadirachtin decomposition are not known with certainty; and (2) in view of the fact that other traditional stabilizing additives, particularly anti-oxidants such as butylated hydroxytoluene and tert-butylhydroquinone, failed to effectively stabilize azadirachtin solutions (Examples 3 and 4).

As noted above, the absolute rate of azadirachtin decomposition is dependent upon the particular solvent and surfactant(s) used. Importantly, however, the stabilizing effect of epoxides is evident regardless of the solvent used and regardless of the presence or type of surfactant. Specifically, epoxidized soybean oil substantially improved the stability of azadirachtin in six formulations comprising different solvents, all with 15% surfactant (Example 6).

The stabilizing effect of epoxides is also evident across a wide range of epoxide concentrations and can be extrapolated to very low concentrations, e.g., less than 1% by weight (Example 7).

Example 8 shows that significant azadirachtin degradation occurs across a broad range of azadirachtin concentrations. Importantly, epoxides enhance the stability of azadirachtin regardless of azadirachtin concentration. The azadirachtin formulation preferably contains between 0.1–85% azadirachtin, and most preferably contains between 1–5% azadirachtin.

The stabilizing agents of the present invention fall within the general class of epoxides, compounds containing the three-membered oxirane ring. Suitable epoxides for use in this invention include, but are not limited to, epoxidized soybean oil, epoxidized linseed oil, 1,2-epoxyoctane, 1,2-epoxy-5,9-cyclododecadiene, epichlorohydrin, 2,3-epoxypropyl-4-methoxyphenylether, cyclooctene oxide, and n-(2,3-epoxypropyl)phthalimide (Example 9). Preferred stabilizing agents include epoxidized vegetable oil. Epoxidized soybean oil is most preferred.

The present invention will become more clear from consideration of the following examples which are set forth to further illustrate the principles of the invention and are not intended, in any way, to be limitative thereof.

EXAMPLES

Example 1

Stability of azadirachtin in various solvents

An azadirachtin-containing neem seed extract was dissolved in suitable solvent to give a final azadirachtin concentration of 3.3±0.2% by weight. The solutions were sealed in vials and heated to 50° C. for six weeks in this accelerated aging study.

Analysis of azadirachtin was by HPLC using an external, analytically pure azadirachtin standard curve as described in, for instance, Uebel, E. C., et al. (1979) "C-18 HPLC," J. Liq. Chromatography 2:875; Warthen, J. D. Jr., et al. (1984) J. Liq. Chromatography 7:591; Yamasaki, R. B., et al. (1986) "Phenyl HPLC," J. Chromatography 356:220; and Huang, H. and Morgan, E. D. (1990) "Supercritical Fluid Chromatography," J. Chromatography 519:137.

As evidenced by Table 1, a substantial decrease in azadirachtin content occurs under accelerated aging conditions, regardless of the solvent used.

TABLE 1

| Solvent | Final % Azadirachtin |
| --- | --- |
| dipropylene glycol | 1.7 |
| n-hexyl alcohol | 1.4 |
| tetrahydrofuryl alcohol | 2.5 |
| gamma-butyrolactone | 0.9 |
| cyclohexanol | 0.3 |
| n-methyl pyrrolidinone | 1.9 |
| methanol | 0.8 |
| isopropanol | 1.3 |
| acetonitrile | 2.7 |
| ethyl acetate | 1.6 |
| ethanol | 0.7 |

Example 2

Stability of azadirachtin in aromatic solvent with various surfactant blends

An azadirachtin-containing neem seed extract was dissolved in aromatic petroleum distillate and surfactant blends were added to a final concentration of 15% by weight. The solutions were sealed in vials and heated to 50° C. for three weeks in this accelerated aging study. Table 2 presents the initial and final azadirachtin concentrations. Azadirachtin analysis as per Example 1. It can be seen that certain surfactant blends substantially increase the rate of azadirachtin degradation.

TABLE 2

| | % Azadirachtin | |
| --- | --- | --- |
| | Initial | Final |
| Aromatic Distillate Only | 3.7 | 3.2 |
| Surfactant Blend 1[1] | 3.1 | 0.2 |
| Surfactant Blend 2[2] | 3.1 | 2.6 |
| Surfactant Blend 3[3] | 3.1 | 2.1 |

[1]Surfactant Blend 1 = sodium dodecyl benzene sulfonate and mixed polyethoxylated alkyl phenols
[2]Surfactant Blend 2 = polyethoxylated alkyl phenols
[3]Surfactant Blend 3 = block copolymers of propylene oxide and ethylene oxide Example 3

Stability of azadirachtin with various additives

An azadirachtin -containing neem seed extract was dissolved in aromatic petroleum distillate, surfactant (15% by weight) and various additive treatments to give a final azadirachtin concentration of 3.1±0.2% by weight. pH was adjusted as indicated with ammonium hydroxide. The solutions were sealed in vials and heated to 50° C. for three weeks in this accelerated aging study. Azadirachtin analysis as per Example 1. It can be seen that only epoxidized soybean oil substantially enhances azadirachtin stability.

TABLE 3

| | Final % Azadirachtin |
| --- | --- |
| no additives | 0.0 |
| pH adjusted to 7 | 1.4 |
| pH adjusted to 8.6 | 1.9 |
| 0.5% by weight BHT[4] | 0.4 |
| 0.5% by weight TBHQ[5] | 0.4 |
| 3.0% by weight ESO[6] | 2.8 |
| 0.5% BHT pH 7 | 1.9 |
| 0.5% TBHQ pH 7 | 2.0 |

[4]BHT = butylated hydroxytoluene
[5]TBHQ = tert-butylhydroquinone
[6]ESO = epoxidized soybean oil Example 4

Stability of azadirachtin with various additives (pH monitored)

An azadirachtin -containing neem seed extract was dissolved in aromatic petroleum distillate, surfactant (15% by weight) and various additive treatments to give a final azadirachtin concentration of 3.5±0.2% by weight. Solutions were sealed in vials and heated to 50° C. for three weeks in this accelerated aging study. Azadirachtin analysis as per Example 1. It be seen that epoxidized soybean oil, added either alone or in combination with butylated hydroxytoluene, enhances azadirachtin stability. Butylated hydroxytoluene alone has no effect on azadirachtin stability.

TABLE 4

| | Initial pH | Final % Azadirachtin |
| --- | --- | --- |
| no additives | 6.0 | 0.3 |
| 3.0% by weight ESO[1] | 6.0 | 2.6 |
| 0.5% by weight BHT[2] | 7.2 | 0.1 |
| 0.5% by weight BHT/ 3.0% by weight ESO | 7.2 | 2.3 |
| 6.0% by weight ESO | 6.0 | 2.5 |
| 4.0% by weight ESO | 7.2 | 2.2 |

[1]ESO = epoxidized soybean oil
[2]BHT = butylated hydroxytoluene

Example 5

Stability of azadirachtin with epoxidized soybean oil and/or non-epoxidized paraffinic oil ("crop oil")

An azadirachtin -containing neem seed extract was dissolved in aromatic petroleum distillate and surfactant blend (15% by weight) with various combinations of epoxidized soybean oil and/or crop oil (non-epoxidized paraffinic oil) to give a final azadirachtin concentration of 3.2±0.2% by weight. In this accelerated aging study, solutions were sealed in vials and heated to various temperatures (25° C., 37° C., 43° C. and 50° C.) for the indicated time intervals. Azadirachtin analysis as per Example 1.

| Formulation A | No additives |
| --- | --- |
| Formulation B | 6.0% by weight epoxidized soybean oil |
| Formulation C | 5.0% by weight crop oil |
| Formulation D | 5.0% by weight crop oil and 3.0% by weight epoxidized soybean oil |

TABLE 5

| | | Azadirachtin Content (% by weight) | | | |
| --- | --- | --- | --- | --- | --- |
| Temperature | Weeks | A | B | C | D |
| 25° C. | 2 | 3.1 | 3.0 | 3.1 | 3.0 |
| | 4 | 3.3 | 3.2 | 3.2 | 3.1 |
| | 8 | 3.2 | 3.6 | 3.4 | 3.2 |
| | 12 | 3.3 | 3.3 | 3.2 | 3.1 |
| | 36 | 3.2 | 3.2 | 3.3 | 3.1 |
| 37° C. | 2 | 3.3 | 3.0 | 3.2 | 2.9 |
| | 4 | 3.3 | 3.1 | 3.2 | 3.0 |
| | 8 | 3.2 | 3.1 | 3.1 | 3.1 |
| | 12 | 3.1 | 3.1 | 3.0 | 2.9 |
| | 36 | 2.1 | 2.8 | 2.2 | 2.3 |
| 43° C. | 2 | 3.1 | 2.8 | 3.0 | 3.0 |
| | 4 | 3.3 | — | 3.1 | 3.0 |
| | 8 | 3.1 | 2.2 | 2.2 | 2.8 |
| | 10 | 3.0 | 2.9 | 2.8 | 3.1 |
| | 12 | 2.9 | 2.8 | 2.7 | 2.7 |
| | 36 | 0.9 | 2.3 | 0.8 | 1.6 |
| 50° C. | 2 | 3.0 | 3.0 | 2.9 | 2.8 |
| | 4 | 2.8 | 2.8 | 2.6 | 2.7 |
| | 8 | 1.8 | 2.5 | 2.4 | 2.8 |

TABLE 5-continued

| Temperature | Weeks | Azadirachtin Content (% by weight) | | | |
|---|---|---|---|---|---|
| | | A | B | C | D |
| | 10 | 1.8 | 2.3 | 1.5 | 1.9 |
| | 12 | 1.4 | 2.2 | 1.1 | 1.9 |

Example 6

Stability of azadirachtin in various solvents with and without epoxidized soybean oil An azadirachtin containing neem seed extract was dissolved in solvent (as listed) and surfactant blend (15% by weight) with and without epoxidized soybean oil (6% by weight) to a final azadirachtin concentration of 3.2±0.2% by weight. The solutions were sealed in vials and heated to 50° C. for eight weeks in this accelerated aging study. Azadirachtin analysis as per Example 1. It can be seen that epoxidized soybean oil stabilizes azadirachtin in solution regardless of solvent type.

TABLE 6

| Solvent | Final % Azadirachtin | |
|---|---|---|
| | Without ESO[1] | With ESO |
| Hexanol | 1.2 | 2.1 |
| Hexylene glycol | 1.4 | 2.4 |
| Aromatic petroleum distillate | 0.9 | 1.7 |
| Dipropylene glycol | 2.0 | 2.9 |
| N-methyl pyrrolidinone | 1.4 | 2.9 |
| Tetrahydrofuryl alcohol | 1.7 | 2.0 |

[1]ESO = epoxidized soybean oil

Example 7

Stability of azadirachtin with increasing epoxidized soybean oil concentrations

An azadirachtin containing neem seed extract was dissolved in aromatic petroleum distillate, surfactant (15% by weight), and various levels of epoxidized soybean oil to a final azadirachtin concentration of 3.3±0.2% by weight. The solutions were sealed in vials and heated to 50° C. for eight weeks in this accelerated aging study. Azadirachtin analysis as per Example 1. It can be seen that the ESO stabilizing effect occurs at a wide range of ESO concentrations and can be extrapolated to very low concentrations, e.g., less than 1% by weight.

TABLE 7

| % ESO[1] | Final % Azadirachtin |
|---|---|
| 0.0 | 1.0 |
| 1.0 | 1.5 |
| 3.0 | 1.6 |
| 6.0 | 1.9 |
| 9.0 | 2.0 |
| 12.0 | 2.2 |

[1]ESO = epoxidized soybean oil

Example 8

Effect of azadirachtin concentration on stability An azadirachtin-containing neem seed extract was dissolved in aromatic petroleum distillate and surfactant (15% by weight) to give solutions ranging from 1.1% to 5.5% azadirachtin by 1.1 weight. The solutions were sealed in vials, heated to 50° C. and assayed after eight weeks in this accelerated aging study. Azadirachtin analysis as per Example 1. It can be seen that significant degradation of azadirachtin occurred across the broad range of levels tested.

TABLE 8

| % Azadirachtin | | |
|---|---|---|
| Initial | Final | % Loss |
| 1.1 | 0.9 | 18 |
| 1.7 | 0.8 | 53 |
| 3.3 | 1.3 | 61 |
| 5.5 | 1.8 | 67 |

Example 9

Stability of azadirachtin with various epoxides

An azadirachtin-containing neem seed extract was dissolved in aromatic petroleum distillate with various epoxides (5% and 10% by weight) to given an azadirachtin concentration of 3.2±0.2% by weight. The solutions were sealed in vials and heated to 50° C. for 28 days in this accelerated aging study. Azadirachtin analysis as per Example 1. As shown in Table 9, the stabilizing effect on azadirachtin occurs with a variety of epoxides.

| A | no epoxide |
|---|---|
| B | epoxidized soybean oil |
| C | epoxidized linseed oil |
| D | 1,2-epoxyoctane |
| E | 1,2-epoxy-5,9-cyclododecadiene |
| F | epichlorohydrin |
| G | 2,3-epoxypropyl-4-methoxyphenylether |
| H | cyclooctene oxide |
| I | N-(2,3-epoxypropyl) phthalimide |

TABLE 9

| Treatment | Final % Azadirachtin | |
|---|---|---|
| | 5% Epoxide | 10% Epoxide |
| A[1] | — | — |
| B | 2.8 | 2.9 |
| C | 2.7 | 2.9 |
| D | 2.7 | 2.8 |
| E | 2.6 | 2.6 |
| F | 2.9 | 3.1 |
| G | 2.8 | 2.8 |
| H | 2.5 | 2.5 |
| I | 2.8 | 3.2 |

[1]Final azadirachtin concentration = 2.4%.

Example 10

Azadirachtin Derivatives

Table 10 presents examples of azadirachtin derivatives encompassed by the present invention. This table is by way of illustration only and is not intended, in any way, to be limitative thereof.

TABLE 10

Azadirachtin Derivatives

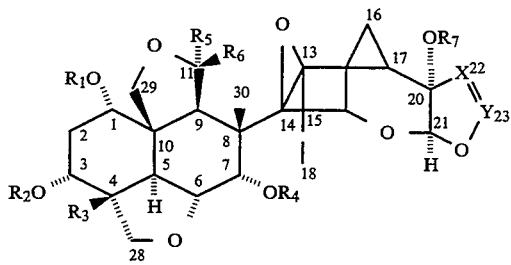

| Compound | $R_1$ | $R_2$ | $R_3$ | $R_4$ | $R_5$ | $R_6$ | $R_7$ | X | Y |
|---|---|---|---|---|---|---|---|---|---|
| Azadirachtin | tiglate | Ac | $CO_2Me$ | H | $CO_2Me$ | OH | H | CH= | =CH |
| Dihydro-azadirachtin | tiglate | Ac | $CO_2Me$ | H | $CO_2Me$ | OH | H | $CH_2$ | $CH_2$ |
| Tetrahydro-azadirachtin | 2-methyl-butyrate | Ac | $CO_2Me$ | H | $CO_2Me$ | OH | H | $CH_2$ | $CH_2$ |
| 3-Deacetyl-azadirachtin | tiglate | H | $CO_2Me$ | H | $CO_2Me$ | OH | H | CH= | =CH |
| 11-Methyl-azadirachtin | tiglate | Ac | $CO_2Me$ | H | $CO_2Me$ | OMe | H | CH= | =CH |
| 11-Acetyl-azadirachtin | tiglate | Ac | $CO_2Me$ | H | $CO_2Me$ | OAc | H | CH= | =CH |
| 23-α-Ethoxy-22,23-dihydro-azadirachtin | tiglate | Ac | $CO_2Me$ | H | $CO_2Me$ | OH | H | $CH_2$ | CH-α-OEt |
| 23-β-Ethoxy-22,23-dihydro-azadirachtin | tiglate | Ac | $CO_2Me$ | H | $CO_2Me$ | OH | H | $CH_2$ | CH-β-OEt |
| 23-α-Methoxy-22,23-dihydro-azadirachtin | tiglate | Ac | $CO_2Me$ | H | $CO_2Me$ | OH | H | $CH_2$ | CH-α-OMe |
| 23-β-Methoxy-22,23-dihydro-azadirachtin | tiglate | Ac | $CO_2Me$ | H | $CO_2Me$ | OH | H | $CH_2$ | CH-β-OMe |
| 23-α-Iso-propoxy-22,23-dihydro-azadirachtin | tiglate | Ac | $CO_2Me$ | H | $CO_2Me$ | OH | H | $CH_2$ | CH-α-O-i-Pr |
| 23-β-Iso-propoxy-22,23-dihydro-azadirachtin | tiglate | Ac | $CO_2Me$ | H | $CO_2Me$ | OH | H | $CH_2$ | CH-β-O-i-Pr |
| 22,23-Dihydro-22-α-bromo-α,β-methoxy-azadirachtin | tiglate | Ac | $CO_2Me$ | H | $CO_2Me$ | OH | H | CH-α-Br | CH—OMe |
| 22,23-Dihydro-22-α-bromo-α,β-ethoxy-azadirachtin | tiglate | Ac | $CO_2Me$ | H | $CO_2Me$ | OH | H | CH-α-Br | CH—OEt |
| 22,23-Dihydro-22-α-bromo-α,β-isopropoxy-azadirachtin | tiglate | Ac | $CO_2Me$ | H | $CO_2Me$ | OH | H | CH-α-Br | CH—O-i-Pr |
| 23-α-Acetoxy-22,23-dihydro-azadirachtin | tiglate | Ac | $CO_2Me$ | H | $CO_2Me$ | OH | H | $CH_2$ | CH-α-OAc |
| 23-β-Acetoxy-22,23-Dihydro-azadirachtin | tiglate | Ac | $CO_2Me$ | H | $CO_2Me$ | OH | H | $CH_2$ | CH-β-OAc |
| 1-Cinnamoyl-azadirachtin | PhCH=CHC(O) | Ac | $CO_2Me$ | H | $CO_2Me$ | OH | H | CH= | =CH |
| 4-Decarbo-methoxy-azadirachtin | tiglate | Ac | Me | H | $CO_2Me$ | OH | H | CH= | =CH |
| 12-Decarbo-methoxy-azadirachtin | tiglate | Ac | $CO_2Me$ | H | H | OH | H | CH= | =CH |
| 3-Tigloyl-azadirachtol | H | tiglate | $CO_2Me$ | H | $CO_2Me$ | H | H | CH= | =CH |
| Tetrahydro-3-tigloyl-azadirachtol | H | 2-methyl-butyrate | $CO_2Me$ | H | $CO_2Me$ | H | H | $CH_2$ | $CH_2$ |
| 1-Detigloyl-29-decarbo-methoxy- | H | Ac | Me | H | $CO_2Me$ | OH | H | CH= | =CH |

TABLE 10-continued

Azadirachtin Derivatives

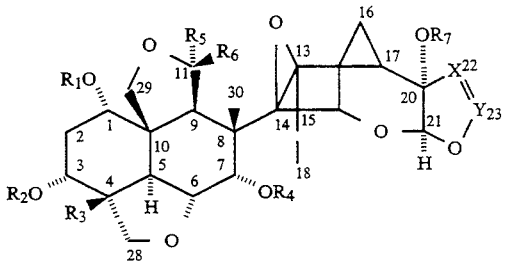

| Compound | R₁ | R₂ | R₃ | R₄ | R₅ | R₆ | R₇ | X | Y |
|---|---|---|---|---|---|---|---|---|---|
| azadirachtin | | | | | | | | | |
| 23-Acetoxy-22,23-dihydro-azadirachtol | H | H | CO₂Me | H | CO₂Me | H | H | CH₂ | CHOAC |
| 11,20-O,O-Dicarbomethoxy-22,23-dihydro-azadirachtin | tiglate | Ac | CO₂Me | H | CO₂Me | OH | H | CH₂ | CH₂ |
| Azadirachtol | H | H | CO₂Me | H | CO₂Me | H | H | CH= | =CH |
| Dihydro-azadirachtol | H | H | CO₂Me | H | CO₂Me | H | H | CH₂ | CH₂ |
| 7,11,20-O,O,O-trimethyl-azadirachtin | tiglate | Ac | CO₂Me | Me | CO₂Me | OMe | Me | CH= | =CH |
| 12,29-Didecarbomethoxy-azadirachtin | tiglate | Ac | Me | H | H | OH | H | CH= | =CH |

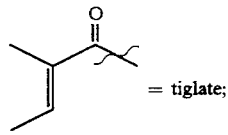
= tiglate;

Ac = CH₃C(O)—;
Me = CH₃—;
Et = CH₃CH₂—;
i-Pr = (CH₃)₂CH—.

Other Azadirachtin Derivatives:

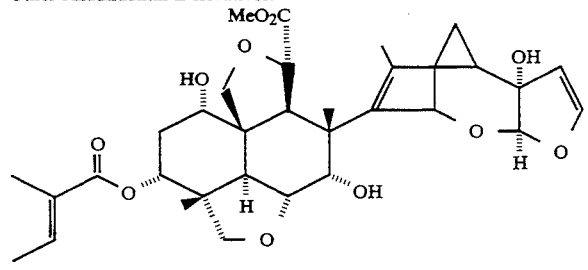

3-Tigloyl-13,14-deepoxyazadirachtol

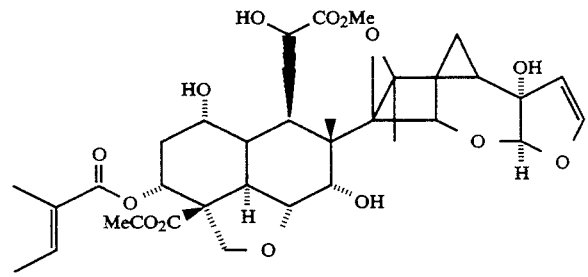

1-hydroxy-3-tigloyl-19-demethyleneoxyazadirachtin

We claim:

1. A storage-stable pesticide composition comprising from about 0.1 percent to about 85 percent azadirachtin and from about 0.1 percent to about 40 percent epoxide, wherein said percentages are on a weight/weight basis.

2. A storage-stable pesticide composition according to claim 1 wherein said epoxide is selected from the group consisting of epoxidized vegetable oil, 1,2-epoxyoctane, 1,2-epoxy-5,9-cyclododecadiene, epichlorohydrin, 2,3-epoxypropyl-4-methoxphenylether, cyclooctene oxide, and N-(2,3-epoxpropyl)-phthalimide.

3. A storage-stable pesticide composition according to claim 1 wherein said epoxide is an epoxidized vegetable oil.

4. An epoxidized vegetable oil according to claim 3 wherein said vegetable oil is epoxidized soybean oil or epoxidized linseed oil.

5. A storage-stable pesticide composition according to claim 1 wherein said azadirachtin is derived from a neem seed extract.

6. A storage-stable pesticide composition according to claim 1 wherein said composition comprises from about 0.1 percent to about 40 percent azadirachtin, wherein said percentages are on a weight/weight basis.

7. A storage-stable pesticide composition according to claim 1 wherein said composition comprises from about 1.0 percent to about 20 percent azadirachtin, wherein said percentages are on a weight/weight basis.

8. A storage-stable pesticide composition according to claim 1 wherein said composition comprises from about 1 percent to about 5 percent azadirachtin, wherein said percentages are on a weight/weight basis.

9. A storage-stable pesticide composition according to claim 1 wherein said composition comprises from about 0.5 percent to about 20 percent epoxide, wherein said percentages are on a weight/weight basis.

10. A storage-stable pesticide composition according to claim 1 further comprising from about 0.2 percent to about 50 percent surfactant, wherein said surfactant is a nonionic surfactant or an anionic/non-ionic surfactant blend, and wherein said percentage is on a weight/weight basis.

11. A storage-stable pesticide composition according to claim 1 further comprising about from 3 percent to about 20 percent surfactant, wherein said surfactant is a non-ionic surfactant or an anionic/non-ionic surfactant blend, and wherein said percentage is on a weight/weight basis.

12. A storage-stable pesticide composition comprising from about 0.1 percent to about 85 percent azadirachtin derivative and from about 0.1 percent to about 40 epoxide, wherein said percentages are on a weight/weight basis .

13. An azadirachtin derivative according to claim 12 wherein said derivative is selected from the group consisting of dihydroazadirachtin, tetrahydroazadirachtin, 3-deacetylazadirachtin, 11-methylazadirachtin, 11-acetylazadirachtin, 23-α-ethoxy-22,23,-dihydroazadirachtin, 23-β-ethoxy-22,23-dihydroazadirachtin, 23-α-methoxy-22, 23 -dihydroazdirachtin, 23-β-methoxy-22,23-dihydroazadirachtin, 23-α-isopropoxy-22,23-dihydroazadirachtin, 23-β-isopropoxy-22,23,-dihydroazadirachtin, 22,23-dihydro-22-α-bromo-α,β-methoxyazadirachtin, 22,23-dihydro-22-α-bromo-α,β-ethoxyazadirachtin, 22,23-dihydro-α-bromo-α,β-isopropoxyazadirachtin, 23-α-acetoxy-22,23-dihydroazadirachtin, 23-β-acetoxy-22,23-dihydroazadirachtin, 1-cinnamoylazadirachtin, 4-decarbomethoxyazadirachtin, 12-decarbomethoxyazadirachtin, 3-tigloylazadirachtol, tetrahydro-3-tigloylazadirachtol, 1-detigloyl-29-decarbomethoxyazadirachtin, azadirachtol, dihydroazadirachtol, 23-acetoxy-22,23-dihydroazadirachtol, 11,20-0,0-dicarbomethoxy-22,23-dihydroazadirachtin, 7,11,20-0,0,0-trimethylazadirachtin, 12,29-didecarbomethoxyazadirachtin, 3-tigloyl-13,14-deepoxyazadirachtol, and 1-hydroxy-3-tigloyl-19-demethyleneoxyazadirachtin.

14. A storage-stable pesticide composition according to claim 12 wherein said epoxide is selected from the group consisting of epoxidized vegetable oil, 1,2-epoxyoctane, 1,2-epoxy-5,9-cyclododecadiene, epichlorohydrin, 2,3-epoxypropyl-4-methoxyphenylether, cyclooctene oxide, and N-(2,3-epoxypropyl)-phthalimide.

15. A storage-stable pesticide composition according to claim 12 wherein said epoxide is an epoxidized vegetable oil.

16. A storage-stable pesticide composition according to claim 15 wherein said epoxidized vegetable oil is epoxidized soybean oil or epoxidized linseed oil.

17. A storage-stable pesticide composition according to claim 12 wherein said composition comprises from about 0.1 percent to about 40 percent azadirachtin derivative, and wherein said percentages are on a weight/weight basis.

18. A storage-stable pesticide composition according to claim 12 wherein said composition comprises from about 0.1 percent to about 20 percent azadirachtin derivative, and wherein said percentages are on a weight/weight basis.

19. A storage-stable pesticide composition according to claim 12 wherein said composition comprises from about 1 percent to about 5 percent azadirachtin derivative, and wherein said percentages are on a weight/weight basis.

20. A storage-stable pesticide composition according to claim 12 wherein said composition comprises from about 0.5 percent to about 20 percent epoxide, and wherein said percentages are on a weight/weight basis.

21. A storage-stable pesticide composition according to claim 12 further comprising about 0.2 percent to about 50 percent surfactant, wherein said surfactant is a non-ionic surfactant or an anionic/non-ionic surfactant blend, and wherein said percentage is on a weight/weight basis.

22. A storage-stable pesticide composition according to claim 12 further comprising from about 3 percent to about 20 percent surfactant, wherein said surfactant is a non-ionic surfactant or an anionic/non-ionic surfactant blend, and wherein said percentage is on a weight/weight basis.

* * * * *

UNITED STATES PATENT AND TRADEMARK OFFICE
CERTIFICATE OF CORRECTION

PATENT NO. : 5,352,697

DATED : Oct. 4, 1994

INVENTOR(S) : Butler et al.

It is certified that error appears in the above-indentified patent and that said Letters Patent is hereby corrected as shown below:

On the cover page, column 1, first cited reference, please rewrite "Hennarf," as --Hennart,--. On the cover page, column 1, line 1, please rewrite "Hennarf," as --Hennart,--. At column 1, line 10, please insert --by-- between "improved" and "adjusting". At column 4, line 42, please rewrite "Biso-" as --B-iso---. At column 4, line 45, please insert --,-- between "tin" and "1-cinnamoylazadirachtin,". At column 4, line 58, please rewrite "Meliceae" as --Meliceae--. At column 5, line 1, please insert --.-- between "20%" and "Suitable". At column , line 66, please begin "An" as a new paragraph. At column 10, line 2, please rewrite "1.1%" as --1.1%--. At column 10, line , please delete "1.1". At column 14 (Table 10), line 17, please rewrite "CHOAC" as --CHOAc--.

Signed and Sealed this

Fifth Day of September, 1995

Attest:

BRUCE LEHMAN

Attesting Officer    Commissioner of Patents and Trademarks